United States Patent [19]
Gough et al.

[11] Patent Number: 5,735,847
[45] Date of Patent: Apr. 7, 1998

[54] MULTIPLE ANTENNA ABLATION APPARATUS AND METHOD WITH COOLING ELEMENT

[75] Inventors: Edward J. Gough, Menlo Park; Alan A. Stein, Moss Beach, both of Calif.

[73] Assignee: ZoMed International, Inc., Mountain View, Calif.

[21] Appl. No.: 576,435

[22] Filed: Dec. 19, 1995

Related U.S. Application Data

[63] Continuation-in-part of Ser. No. 515,379, Aug. 15, 1995.
[51] Int. Cl.$^6$ ...................... A61B 17/39
[52] U.S. Cl. ............ 606/41; 606/42; 606/48; 606/45; 606/15; 607/101; 607/102
[58] Field of Search ............ 606/41, 42, 45–50, 606/13–15; 607/100–102, 122, 154, 156; 128/642

[56] References Cited

U.S. PATENT DOCUMENTS

| | | |
|---|---|---|
| Re. 32,057 | 12/1985 | Leveen . |
| Re. 32,066 | 1/1986 | Leveen . |
| 3,991,770 | 11/1976 | Leveen . |
| 4,016,886 | 4/1977 | Doss . |
| 4,043,342 | 8/1977 | Morrison, Jr. . |
| 4,074,718 | 2/1978 | Morrison, Jr. . |
| 4,080,959 | 3/1978 | Leveen . |
| 4,095,602 | 6/1978 | Leveen . |
| 4,119,102 | 10/1978 | Leveen . |
| 4,140,130 | 2/1979 | Storm, III . |
| 4,154,246 | 5/1979 | Leveen . |
| 4,230,129 | 10/1980 | Leveen . |
| 4,285,346 | 8/1981 | Armitage . |
| 4,290,435 | 9/1981 | Waggott . |
| 4,303,636 | 12/1981 | Gordon . |
| 4,346,715 | 8/1982 | Cammell . |
| 4,375,220 | 3/1983 | Matvias . |
| 4,545,368 | 10/1985 | Rand et al. . |
| 4,565,200 | 1/1986 | Cosman . |
| 4,574,782 | 3/1986 | Borrelli . |
| 4,586,490 | 5/1986 | Katz . |
| 4,676,258 | 6/1987 | Inokuchi et al. . |
| 4,709,701 | 12/1987 | Weber . |
| 4,763,671 | 8/1988 | Goffinet . |
| 4,800,899 | 1/1989 | Elliott . |
| 4,813,429 | 3/1989 | Eshel . |
| 4,823,791 | 4/1989 | D'Amelio . |
| 4,860,744 | 8/1989 | Johnson . |
| 4,881,543 | 11/1989 | Trembly et al. . |
| 4,887,614 | 12/1989 | Shirakami et al. . |
| 4,920,978 | 5/1990 | Colvin . |
| 4,931,047 | 6/1990 | Broadwin . |
| 4,945,912 | 8/1990 | Langberg . |
| 4,947,842 | 8/1990 | Marchosky . |
| 4,962,761 | 10/1990 | Golden . |
| 4,976,680 | 12/1990 | Hayman . |
| 4,976,711 | 12/1990 | Parins . |
| 4,983,159 | 1/1991 | Rand . |
| 5,003,991 | 4/1991 | Takayama et al. . |
| 5,007,908 | 4/1991 | Rydell . |
| 5,009,656 | 4/1991 | Reimels . |
| 5,010,897 | 4/1991 | Leveen . |
| 5,047,027 | 9/1991 | Rydell . |
| 5,057,107 | 10/1991 | Parins . |

(List continued on next page.)

*Primary Examiner*—Jennifer Bahr
*Assistant Examiner*—Michael Peffley
*Attorney, Agent, or Firm*—Wilson, Sonsini, Goodrich & Rosati

[57] ABSTRACT

An ablation apparatus includes a multiple antenna device coupled to an electromagnetic energy source that produces an electromagnetic energy ablation output. The multiple antenna device includes a primary antenna with a lumen and a longitudinal axis, and a secondary antenna deployable from the lumen in a lateral direction relative to the longitudinal axis. At least a distal end of each secondary antenna is structurally less rigid than the primary antenna, and the primary antenna is sufficiently rigid to be introduced through tissue. At least one cable coupling the multiple antenna device to the energy source. A cooling element is coupled to the primary antenna. A variety of energy sources can be used including RF, microwave and laser.

51 Claims, 9 Drawing Sheets

U.S. PATENT DOCUMENTS

| | | |
|---|---|---|
| 5,067,952 | 11/1991 | Gudov . |
| 5,071,419 | 12/1991 | Rydell . |
| 5,078,717 | 1/1992 | Parins . |
| 5,085,659 | 2/1992 | Rydell et al. . |
| 5,099,756 | 3/1992 | Franconi . |
| 5,100,423 | 3/1992 | Fearnot . |
| 5,122,137 | 6/1992 | Lennox . |
| 5,125,928 | 6/1992 | Parins . |
| 5,190,517 | 3/1993 | Zieve et al. . |
| 5,190,541 | 3/1993 | Abele . |
| 5,197,466 | 3/1993 | Marchosky . |
| 5,197,963 | 3/1993 | Parins . |
| 5,197,964 | 3/1993 | Parins . |
| 5,203,782 | 4/1993 | Gudov . |
| 5,217,458 | 6/1993 | Parins . |
| 5,236,410 | 8/1993 | Granov . |
| 5,246,438 | 9/1993 | Langberg . |
| 5,257,451 | 11/1993 | Edwards . |
| 5,273,535 | 12/1993 | Edwards . |
| 5,275,162 | 1/1994 | Edwards . |
| 5,277,696 | 1/1994 | Hagen . |
| 5,281,217 | 1/1994 | Edwards . |
| 5,281,218 | 1/1994 | Imran . |
| 5,282,797 | 2/1994 | Chess . |
| 5,290,286 | 3/1994 | Parins . |
| 5,293,869 | 3/1994 | Edwards . |
| 5,295,955 | 3/1994 | Rosen . |
| 5,309,910 | 5/1994 | Edwards . |
| 5,313,943 | 5/1994 | Houser . |
| 5,314,466 | 5/1994 | Stern . |
| 5,328,467 | 7/1994 | Edwards . |
| 5,334,193 | 8/1994 | Nardella . |
| 5,334,206 | 8/1994 | Daikuzono ........................ 606/7 |
| 5,342,357 | 8/1994 | Nardella . |
| 5,348,554 | 9/1994 | Imran et al. . |
| 5,363,861 | 11/1994 | Edwards . |
| 5,366,490 | 11/1994 | Edwards . |
| 5,368,592 | 11/1994 | Stern . |
| 5,370,675 | 12/1994 | Edwards . |
| 5,370,678 | 12/1994 | Edwards . |
| 5,383,917 | 1/1995 | Desai . |
| 5,385,544 | 1/1995 | Edwards et al. ................... 604/22 |
| 5,398,683 | 3/1995 | Edwards . |
| 5,409,453 | 4/1995 | Lundquist . |
| 5,421,819 | 6/1995 | Edwards . |
| 5,423,807 | 6/1995 | Milder . |
| 5,423,808 | 6/1995 | Edwards . |
| 5,423,811 | 6/1995 | Imran et al. . |
| 5,433,708 | 7/1995 | Nichols . |
| 5,435,805 | 7/1995 | Edwards . |
| 5,437,662 | 8/1995 | Nardella . |
| 5,456,662 | 10/1995 | Edwards . |
| 5,456,682 | 10/1995 | Edwards . |
| 5,458,596 | 10/1995 | Lax . |
| 5,458,597 | 10/1995 | Edwards . |
| 5,462,521 | 10/1995 | Bruckner et al. . |
| 5,470,308 | 11/1995 | Edwards . |
| 5,470,309 | 11/1995 | Edwards . |
| 5,471,982 | 12/1995 | Edwards . |
| 5,472,441 | 12/1995 | Edwards . |
| 5,484,400 | 1/1996 | Edwards . |
| 5,486,161 | 1/1996 | Lax . |
| 5,500,012 | 3/1996 | Brucker et al. ................... 607/122 |
| 5,505,730 | 4/1996 | Edwards . |
| 5,507,743 | 4/1996 | Edwards et al. ................... 606/41 |
| 5,509,419 | 4/1996 | Edwards . |
| 5,514,130 | 5/1996 | Baker . |
| 5,514,131 | 5/1996 | Edwards . |
| 5,531,676 | 7/1996 | Edwards . |
| 5,531,677 | 7/1996 | Lundquist et al. . |
| 5,536,240 | 7/1996 | Edwards . |
| 5,536,267 | 7/1996 | Edwards et al. ................... 606/41 |
| 5,540,655 | 7/1996 | Edwards . |
| 5,542,915 | 8/1996 | Edwards . |
| 5,542,916 | 8/1996 | Hirsch . |
| 5,542,928 | 8/1996 | Evans . |
| 5,545,161 | 8/1996 | Imran . |
| 5,545,171 | 8/1996 | Sharkey . |
| 5,545,193 | 8/1996 | Fleischman . |
| 5,546,267 | 8/1996 | Frederiksen . |
| 5,549,108 | 8/1996 | Edwards . |
| 5,549,644 | 8/1996 | Lundquist . |
| 5,554,110 | 9/1996 | Edwards . |
| 5,556,377 | 9/1996 | Rosen . |
| 5,558,672 | 9/1996 | Edwards . |
| 5,558,673 | 9/1996 | Edwards . |
| 5,560,358 | 10/1996 | Arnold et al. . |
| 5,562,703 | 10/1996 | Desai . |

MULTIPLE ANTENNA ABLATION APPARATUS AND METHOD WITH COOLING ELEMENT

REFERENCE TO RELATED APPLICATION

This application is a continuation-in-part of U.S. patent application No. 08/515,379, filed Aug. 15, 1995, still pending, entitled "Multiple Antenna Ablation Apparatus", incorporated herein by reference.

BACKGROUND OF THE INVENTION

1. Field of Invention

This invention relates generally to an ablation apparatus including a multiple antenna device with a primary antenna, a secondary antenna deployed from a primary antenna lumen, and more particularly to a multiple antenna RF apparatus with primary and secondary antennas and a cooling element coupled to the primary antenna.

2. Description of the Related Art

Current open procedures for treatment of tumors are extremely disruptive and cause a great deal of damage to healthy tissue. During the surgical procedure, the physician must exercise care in not cutting the tumor in a manor that creates seeding of the tumor, resulting in metastasis. In recent years, development of products has been directed with an emphasis on minimizing the traumatic nature of traditional surgical procedures.

There has been a relatively significant amount of activity in the area of hyperthermia as a tool for treatment of tumors. It is known that elevating the temperature of tumors is helpful in the treatment and management of cancerous tissues. The mechanisms of selective cancer cell eradication by hyperthermia are not completely understood. However, four cellular effects of hyperthermia on cancerous tissue have been proposed, (i) changes in cell or nuclear membrane permeability or fluidity, (ii) cytoplasmic lysomal disintegration, causing release of digestive enzymes, (iii) protein thermal damage affecting cell respiration and the synthesis of DNA or RNA and (iv) potential excitation of immunologic systems. Treatment methods for applying heat to tumors include the use of direct contact radio-frequency (RF) applicators, microwave radiation, inductively coupled RF fields, ultrasound, and a variety of simple thermal conduction techniques.

Among the problems associated with all of these procedures is the requirement that highly localized heat be produced at depths of several centimeters beneath the surface of the skin.

Attempts to use interstitial local hyperthermia have not proven to be very successful. Results have often produced nonuniform temperatures throughout the tumor. It is believed that tumor mass reduction by hyperthermia is related to thermal dose. Thermal dose is the minimum effective temperature applied throughout the tumor mass for a defined period of time. Because blood flow is the major mechanism of heat loss for tumors being heated, and blood flow varies throughout the tumor, more even heating of tumor tissue is needed to ensure effective treatment.

The same is true for ablation of the minor itself through the use of RF energy. Different methods have been utilized for the RF ablation of masses such as tumors. Instead of heating the tumor it is ablated through the application of energy. This process has been difficult to achieve due to a variety of factors including, (i) positioning of the RF ablation electrodes to effectively ablate all of the mass, (ii) introduction of the RF ablation electrodes to the tumor site and (iii) controlled delivery and monitoring of RF energy to achieve successful ablation without damage to non-tumor tissue.

Thus, non-invasive procedures for providing heat to internal tissue have had difficulties in achieving substantial specific and selective treatment.

Examples illustrating the use of electromagnetic energy to ablate tissue are disclosed in: U.S. Pat. No. 4,562,200; U.S. Pat. No. 4,411,266; U.S. Pat. No. 4,838,265; U.S. Pat. No. 5,403,311; U.S. Pat. No. 4,011,872; U.S. Pat. No. 5,385,544; and U.S. Pat. No. 5,385,544.

There is a need for a multiple antenna ablation apparatus including a primary antenna and secondary antennas, with a cooling element coupled to the primary antenna. There is a further need for a multiple antenna ablation apparatus, with a cooling medium that cools tissue adjacent to the ablation energy delivery surfaces of the apparatus, to reduce charring of an electrode ablation energy delivery surfaces.

SUMMARY OF THE INVENTION

Accordingly, it is an object of the invention is to provide an ablation device which is introduced into a selected tissue mass and provides controlled delivery of electromagnetic energy to the selected tissue mass to reduce antenna electromagnetic delivery surfaces from impeding out Another object of the invention is to provide an ablation device with primary and secondary antennas, and an electromagnetic energy delivery surface of the primary antenna is cooled to reduce it from impeding out.

Yet another object of the invention is to provide an ablation device with a primary antenna that pierces and advances through tissue, secondary electrodes positioned in a primary antenna lumen that are laterally deployed from the primary antenna into a selected tissue mass, and a cooling element that cools an antenna ablation surface.

Yet another object of the invention is to provide an ablation device with a primary antenna that advances through tissue, secondary antennas positioned in a primary antenna lumen with distal ends that are structurally less rigid than the primary antenna, and a cooling element that cools an antenna ablation surface.

A further object of the invention is to provide a monopolar ablation device with primary and secondary antennas, and a cooling element.

Yet another object of the invention is to provide an ablation device with primary and secondary antennas, a cooling element, and the antennas provide ablation in a direction from an interior to an exterior of the selected tissue mass.

Still a further object of the invention is to provide a method for ablating a selected tissue mass by introducing an ablation apparatus with primary and secondary electrodes with a cooling element into the selected tissue mass.

These and other objectives are achieved in an ablation apparatus including a multiple antenna device coupled to an electromagnetic energy source that produces an electromagnetic energy ablation output. The multiple antenna device includes a primary antenna with a lumen and a longitudinal axis, and a secondary antenna deployable from the lumen in a lateral direction relative to the longitudinal axis. At least a distal end of each secondary antenna is structurally less rigid than the primary antenna, and the primary antenna is sufficiently rigid to be introduced through tissue. At least one cable couples the multiple antenna device to the energy source. A cooling element is coupled to the primary antenna.

The present invention is also a method for creating an ablation volume in a selected tissue mass. An ablation device is provided with a primary antenna, one or more deployable secondary antennas housed in a primary antenna lumen formed in the primary antenna, a cooling element coupled to the primary antenna and an energy source coupled to the antennas to deliver electromagnetic energy. The primary antenna is inserted into the selected tissue mass. At least one secondary antenna is deployed into the selected tissue mass from the primary antenna lumen in a lateral direction relative to a longitudinal axis of the primary antenna. An ablation surface of the primary antenna is cooled. Electromagnetic energy is delivered from one of the primary antenna ablation surface, a secondary antenna ablation surface or both to the selected tissue mass. An ablation volume is then created in the selected tissue mass.

The multiple antenna device can be an RF, microwave, short wave antenna and the like. At least two secondary antennas can be included and be laterally deployed from the primary antenna. The secondary antenna is retractable into the primary antenna, permitting repositioning of the primary antenna. When the multiple antenna is an RF antenna, it can be operated in monopolar or bipolar modes, and is capable of switching between the two.

Further, the multiple antenna device can be a multi-modality apparatus. One or all of the antennas can be hollow to receive an infusion medium from an infusion source and introduce the infusion medium into a selected tissue mass.

The cooling element can be a structure that is at least partially positioned in an interior of the primary electrode. The structure can be a tube that includes a hollow lumen adapted to receive a cooling medium. Cooling medium is circulated through the hollow lumen. The distal end of the primary antenna can be open or closed. If it is open, then the cooling element may be a closed container positioned in the interior of the primary antenna. The same is true for the secondary antennas.

Additionally, the cooling element can be positioned at an exterior surface of the antennas or between the walls defining the antennas.

As electromagnetic energy, including but not limited to RF, is delivered to a selected tissue mass, the tissue adjacent to the antennas delivering the electromagnetic energy begins to return the electromagnetic energy to the antennas. This causes a charring of the antennas and a loss of conductivity. By delivering a cooling medium, the tissue adjacent to the antenna delivering the electromagnetic energy is not ablated too rapidly and the antenna can complete its ablation of the targeted site without become too charred and be rendered ineffective. Thus, the delivery of useful electromagnetic energy is not affected and the desired overall tissue site is ablated.

DETAILED DESCRIPTION

Figure 1:
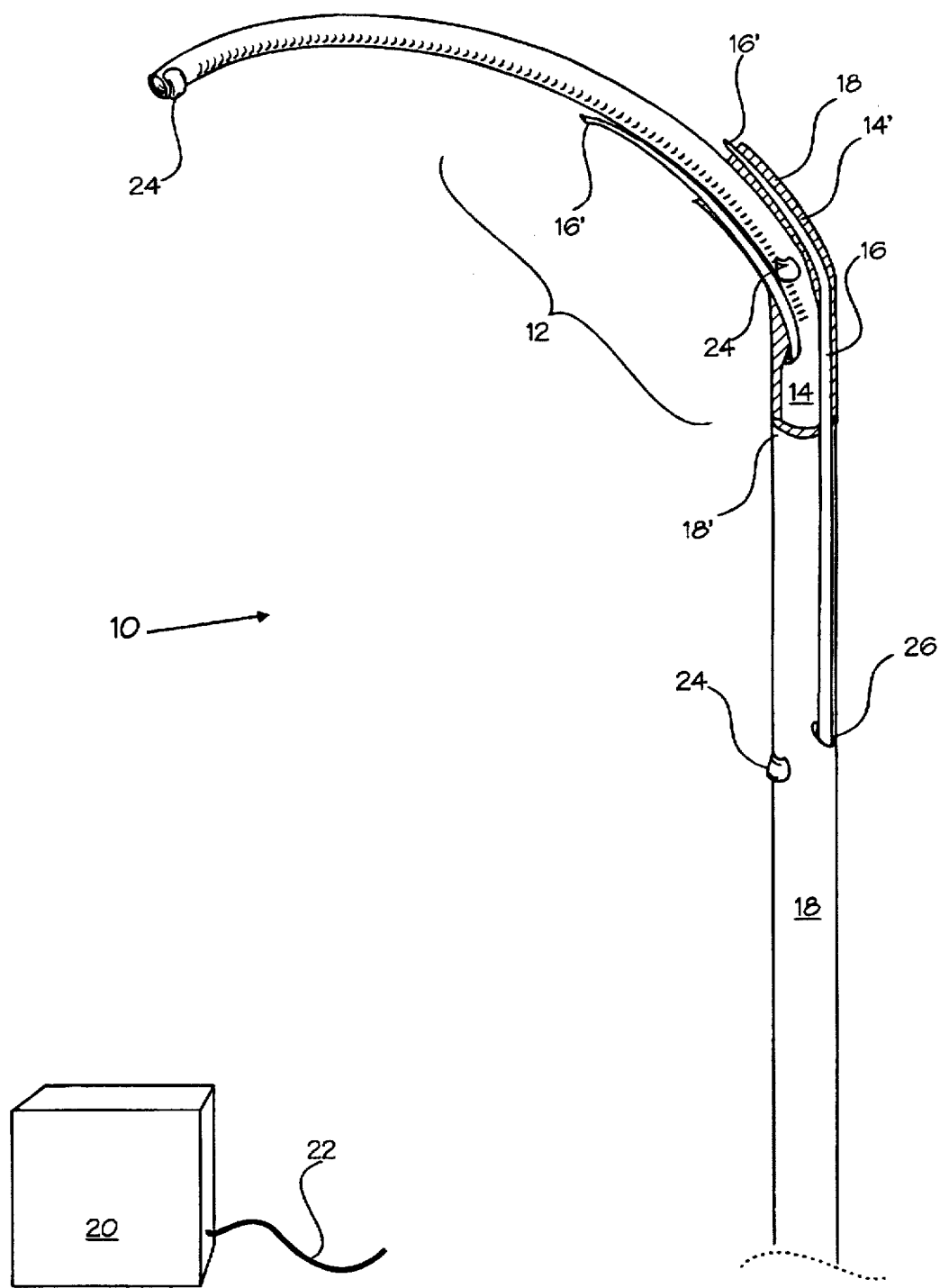
FIG. 1 is a perspective view of the multiple antenna ablation apparatus of the present invention illustrating a primary antenna and a single laterally deployed secondary antenna.

As shown in FIG. 1, an ablation treatment apparatus 10 includes a multiple antenna device 12. Multiple antenna device 12 includes a primary antenna 14, and one or more secondary antennas 16, which are typically electrodes. Secondary antennas 16 are initially positioned in a primary antenna lumen when primary antenna 14 is advanced through tissue. When primary antenna 14 reaches a selected tissue ablation site in a selected tissue mass, including but not limited to a solid lesion, secondary antennas 16 are laterally deployed from the primary antenna lumen and into the selected tissue mass. Ablation proceeds from the interior of the selected tissue mass in a direction towards a periphery of the selected tissue mass.

Each primary and secondary antenna 14 and 16 has an exterior ablation surface which delivers electromagnetic energy to the selected tissue mass. The length and size of each ablation surface can be variable. The length of primary antenna ablation surface relative to secondary antenna ablation surface can be 20% or greater, 33 and ⅓% or greater, 50% or greater, 75% or greater, about the same length, or greater than the length of secondary electrode ablation surface. Lengths of primary and secondary antennas 14 and 16 can be adjustable. Primary antenna 14 can be moved up and down, rotated about its longitudinal axis, and moved back and forth, in order to define, along with sensors, the periphery or boundary of the selected tissue mass, including but not limited to a tumor. This provides a variety of different geometries, not always symmetrical, that can be ablated. The ablation can be between the ablation surfaces of primary and secondary antennas 14 and 16 when operated in a monopolar mode with a ground pad.

Primary antenna 14 is constructed so that it can be introduced percutaneously or laparoscopically through tissue without an introducer. Primary antenna 14 combines the function of an introducer and an electrode. Primary antenna 14 can have a sharpened distal end 14' to assist introduction through tissue. Each secondary antenna 16 has a distal end 16' that is constructed to be less structurally rigid than primary antenna 14. Distal end 16' is that section of secondary antenna 16 that is advanced from the lumen antenna 14 and into the selected tissue mass. Distal end is typically less structurally rigid that primary antenna 14. However, even though sections of secondary antenna 16 which are not advanced through the selected tissue mass may be less structurally rigid than primary antenna 14.

Structurally rigidity is determined by, (i) choosing different materials for antenna 14 and distal end 16' or some greater length of secondary antenna 16, (ii) using the same material but having less of it for secondary antenna 16 or distal end 16', e.g., secondary antenna 16 or distal end 16' is not as thick as primary electrode 14, or (iii) including another material in one of the antennas 14 or 16 to vary their structural rigidity. For purposes of this disclosure, structural rigidity is defined as the amount of deflection that an antenna has relative to its longitudinal axis. It will be appreciated that a given antenna will have different levels of rigidity depending on its length.

Primary and secondary antennas 14 and 16 can be made of a variety of conductive materials, both metallic and non-metallic. One suitable material is type 304 stainless steel of hypodermic quality. In some applications, all or a portion of secondary electrode 16 can be made of a shaped memory metal, such as NiTi, commercially available from Raychem Corporation, Menlo Park, Calif.

Each of primary or secondary antennas 14 or 16 can have different lengths. The lengths can be determined by the actual physical length of an antenna, the amount of an antenna that has an ablation delivery surface, and the length of an antenna that is not covered by an insulator. Suitable lengths include but are not limited to 17.5 cm, 25.0 cm, and 30.0 cm. The actual length of an antenna depends on the location of the selected tissue mass to be ablated, its distance from the skin, its accessibility as well as whether or not the physician chooses a laproscopic, percutaneous or other procedure. Further, ablation treatment apparatus 10, and more particularly multiple antenna device 12, can be introduced through a guide to the desired tissue mass site.

An insulation sleeve 18 may be positioned around an exterior of one or both of the primary and secondary antennas 14 and 16 respectively. Preferably, each insulation sleeve 18 is adjustably positioned so that the length of an antenna ablation surface can be varied. Each insulation sleeve 18 surrounding a primary antenna 14 can include one or more apertures. This permits the introduction of a secondary antenna 16 through primary antenna 14 and insulation sleeve 18.

In one embodiment, insulation sleeve 18 can comprise a polyamide material. A sensor 24 may be positioned on top of polyimide insulation sleeve 18. The polyamide insulation sleeve 18 is semi-rigid. Sensor 24 can lay down substantially along the entire length of polyamide insulation sleeve 18. Primary antenna 14 is made of a stainless-steel hypodermic tubing with 2 cm of exposed ablation surface. Secondary antennas 16 have distal ends 16' that are made of NiTi hypodermic tubing. A handle is included with markings to show the varying distance of secondary antennas 16 from primary antenna 14. Fluid infusion is delivered through a Luer port at a side of the handle. Type-T thermocouples are positioned at distal ends 16'.

An energy source 20 is connected to multiple antenna device 12 with one or more cables 22. Energy source 20 can be an RF source, microwave source, short wave source, laser source and the like. Multiple antenna device 12 can be comprised of primary and secondary antennas 14 and 16 that are RF electrodes, microwave antennas, as well as combinations thereof. Energy source 20 may be a combination RF/microwave box. Further a laser optical fiber, coupled to a laser source 20 can be introduced through one or both of primary or secondary antennas 14 and 16. One or more of the primary or secondary antennas 14 and 16 can be an arm for the purposes of introducing the optical fiber.

Antennas 14 and 16 may be electromagnetically coupled by wiring, soldering, connection to a common couplet, and the like. This permits only one antenna 14 or 16 to be coupled to energy source 20 and use of a single cable 22.

One or more sensors 24 may be positioned on interior or exterior surfaces of primary antenna 14, secondary antenna 16 or insulation sleeve 18. Preferably sensors 24 are positioned at primary antenna distal end 14', secondary antenna distal end 16' and insulation sleeve distal end 18'. Sensors 24 permit accurate measurement of temperature at a tissue site in order to determine, (i) the extent of ablation, (ii) the amount of ablation, (iii) whether or not further ablation is needed and (iv) the boundary or periphery of the ablated mass. Further, sensors 24 prevent non-targeted tissue from being destroyed or ablated.

Sensors 24 are of conventional design, including but not limited to thermistors, thermocouples, resistive wires, and the like. Suitable thermal sensors 24 include a T type thermocouple with copper constantene, J type, E type, K type, fiber optics, resistive wires, thermocouple IR detectors, and the like. It will be appreciated that sensors 24 need not be thermal sensors.

Sensors 24 measure temperature and/or impedance to permit monitoring and a desired level of ablation to be achieved without destroying too much tissue. This reduces damage to tissue surrounding the targeted mass to be ablated. By monitoring the temperature at various points within the interior of the selected tissue mass, a determination of the selected tissue mass periphery can be made, as well as a determination of when ablation is complete. If at any time sensor 24 determines that a desired ablation temperature is exceeded, then an appropriate feedback signal is received at energy source 20 which then regulates the amount of energy delivered to primary and/or secondary antennas 14 and 16.

Thus the geometry of the ablated mass is selectable and controllable. Any number of different ablation geometries can be achieved. This is a result of having variable lengths for primary antenna 14 and secondary antenna 16 ablation surfaces as well as the inclusion of sensors 24.

Preferably, distal end 16' is laterally deployed relative to a longitudinal axis of primary antenna 14 out of an aperture 26 formed in primary antenna 14. Aperture 26 is at distal end 14' or formed in a side of an exterior of antenna 14.

A method for creating an ablation volume in a selected tissue mass includes inserting and advancing primary antenna 14 through tissue and into a selected tissue mass. Secondary antennas 16 are positioned in a lumen formed in antenna 14 while antenna 14 is advanced through tissue. At least one distal end 16' is deployed from the primary antenna lumen into the selected tissue mass in a lateral direction relative to the longitudinal axis of primary antenna 14. Electromagnetic energy is delivered from one of a primary antenna ablation surface, a secondary antenna ablation surface or both to the selected tissue mass. An ablation volume is created in the selected tissue mass. When operated in the monopolar mode, the ablation is between the ablation surfaces of the antennas.

There is wide variation in the amount of deflection of secondary antenna 16. For example, secondary antenna 16 can be deflected a few degrees from the longitudinal axis of primary antenna 14, or secondary antenna can be deflected in any number of geometric configurations, including but not limited to a "J" hook. Further, secondary antenna 16 is capable of being introduced from primary antenna 14 a few millimeters from primary antenna, or a much larger distance. Ablation by secondary antenna 16 can begin a few millimeters away from primary antenna 14, or secondary electrode 16 can be advanced a greater distance from primary antenna 14 and at that point the initial ablation by secondary antenna 16 begins.

Figure 2A:
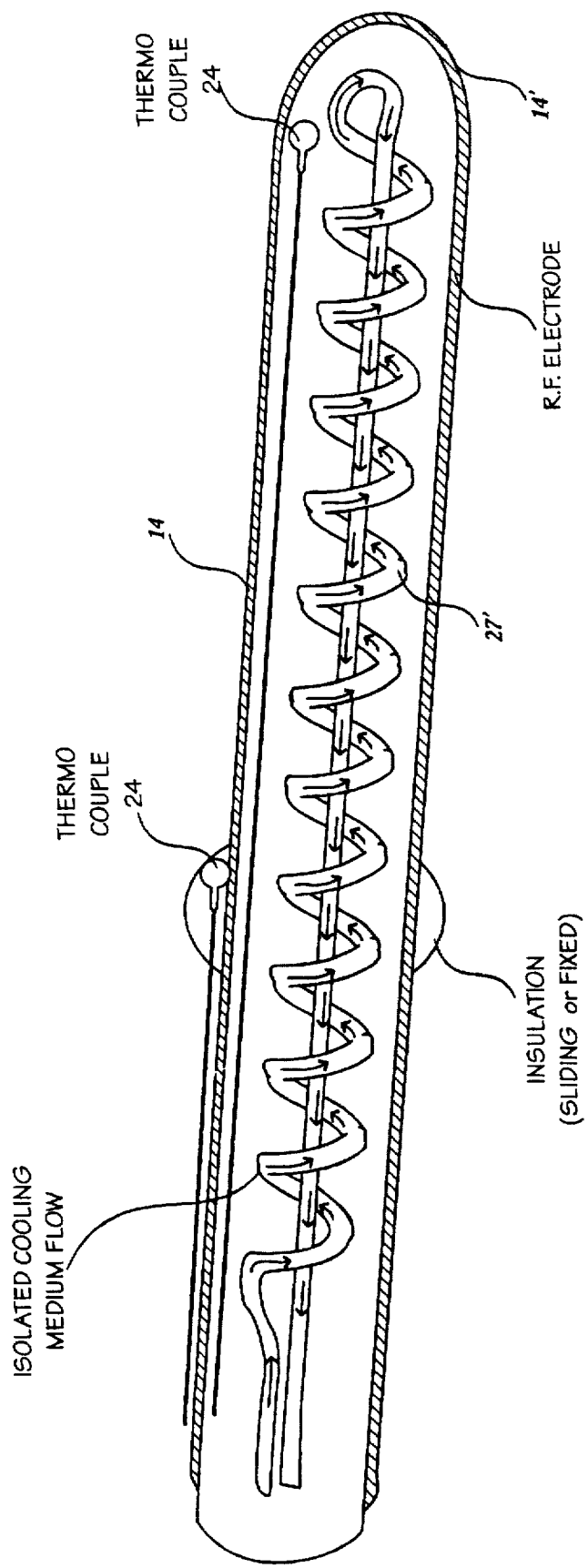
FIG. 2(a) is a cross-sectional view of the primary antenna with a closed distal end and a cooling element positioned in a central lumen of the primary antenna.

As illustrated in FIG. 2(a), primary antenna 14 can include one or more cooling elements 27. One embodiment of a suitable cooling element 27 is a closed elongated structure 27' coupled to a circulating system to introduce a cooling medium. Two lumens can be incorporated with primary antenna 14, or secondary antenna 16, to carry a cooling medium to and away from antennas 14 or 16. In one embodiment, the dimensions are the lumens are; outer lumen 0.117 inches outer diameter by 0.088 inches inner diameter, and inner lumen 0.068 inches outer diameter by 0.060 inner diameter. The cooling medium enters primary antenna 14, absorbs heat generated in the tissue surrounding primary antenna 14, and the heated medium then exits antenna 14. This may be achieved by the use of the two lumens, one introducing the cooling medium, and the other lumen removing heated cooling solution. Heat is subsequently removed from the heated medium, and once again cooled medium is recirculated through antenna 14. This is a continuous process. Cooling element 27 need only be positioned, and provide the cooling function, along that section of antenna 14 which has an ablation energy delivery surface. Insulation sleeve 18 can be slideably adjustable along the length of primary antenna 14 or be in a fixed positioned. The exterior of primary antenna 14 which is not covered by insulation sleeve 18 provides the ablation energy delivery surface. It is only this surface which becomes heated and charred from electromagnetic energy delivered to adjacent tissue. Thus it is only necessary to cool this surface of antenna 14, and the actual cooling by cooling medium 17 can be limited to the ablation energy delivery surface.

Cooling medium may be a refrigerant including but not limited to ethyl alcohol, freon, polydimethlsiloxane, and the like. Cooling can also be achieved with gas expansion cooling by the Joule-Thompson effect.

In another embodiment of cooling element 27, distal end 14' is again closed, and a cooling medium 27 flows through the central lumen formed in antenna 14. The cooling medium 27 is coupled to a recirculation system, which may be a heat exchanger with a pump. The rate of fluid flow through primary antenna 14 is variable based on a number of different parameters.

Figure 2B:
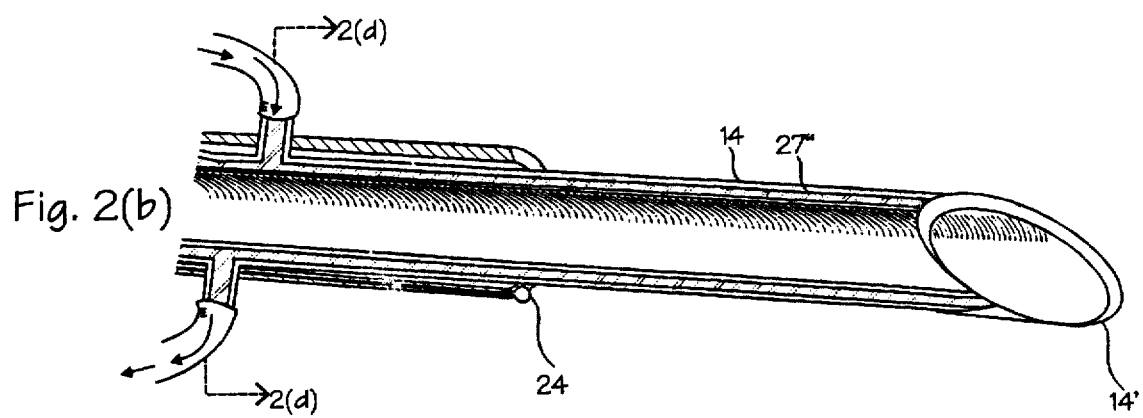
FIG. 2(b) is a cross-sectional view of the primary antenna with an open distal end and a elongated cooling element positioned in the central lumen of the primary antenna.
Figure 2C:
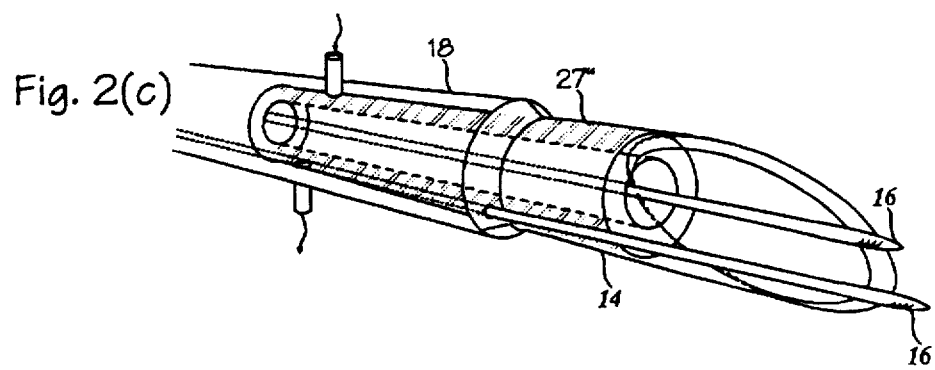
FIG. 2(c) is distal end view of the apparatus of FIG. 2(b).

In yet another embodiment, cooling element 27 is an elongated structure 27", including but not limited to a tubular member such as a cylinder, with a cooling medium flowing through elongated structure 27" (FIG. 2(b)). Elongated structure 27" is positioned within the central lumen of primary antenna 14 and can extend to distal end 14'. Distal end 14' can be open or closed. Cooling medium is confined within elongated structure 27". This permits the introduction and flow of other mediums through the hollow lumen of primary antenna 14. Secondary antennas 16 can exit at distal end 14', or alternatively, they may also exit along a side of antenna 14 (FIG. 2(c)).

Figure 2D:
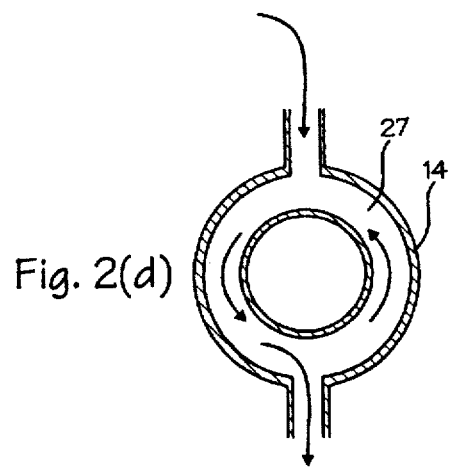
FIG. 2(d) is a cross-sectional view of the apparatus of FIG. 2(b) taken along the lines 2(d)—2(d).

Cooling medium flow through cooling element 27 can introduced through a first port, and exit through a second port (FIG. 2(d)).

A variety of different cooling mediums can be used including but not limited to gas, cooled air, refrigerated air, compressed air, freon, water, alcohol, and the like. Additionally, cooling element 27 can be incorporated into the walls defining primary antenna 14, and may also be positioned at the exterior of primary antenna 14. The desired cooling affect can be achieved without recirculation of the cooling medium. A chiller can also be utilized. The combination of flow rate of cooling medium and temperature is important to achieve a desired level of cooling.

As the amount of cooling increases, the more RF energy effects can be distributed over a larger area. Cooling is provided and controlled until the end of the ablation, at which time the tissue adjacent to antennas 14 and 16 is then ablated. The RF radiation effect on tissue is controlled by the cooling conductive effect.

Cooling element 27 can also be included with secondary antennas 16, as implemented with primary antenna 14.

Electromagnetic energy delivered through primary or secondary antennas 14 or 16 causes the tissue adjacent to the antenna with the ablation energy delivery surface to heat, and return the heat to the antenna 14 and 16. As more heat is applied and returned, the charring effect of antenna 14 and 16 increases. This can result in a loss of electromagnetic energy conductivity through the antennas. The inclusion of cooling element 27 does not affect the effective delivery of electromagnetic energy to a targeted mass. Cooling element 27 permits the entire targeted mass to be ablated while reducing or eliminating the heating of adjacent tissue to antennas 14 and 16. Cooling is only necessary where there is an exposed antenna 14 and 16 surface.

Figure 3:
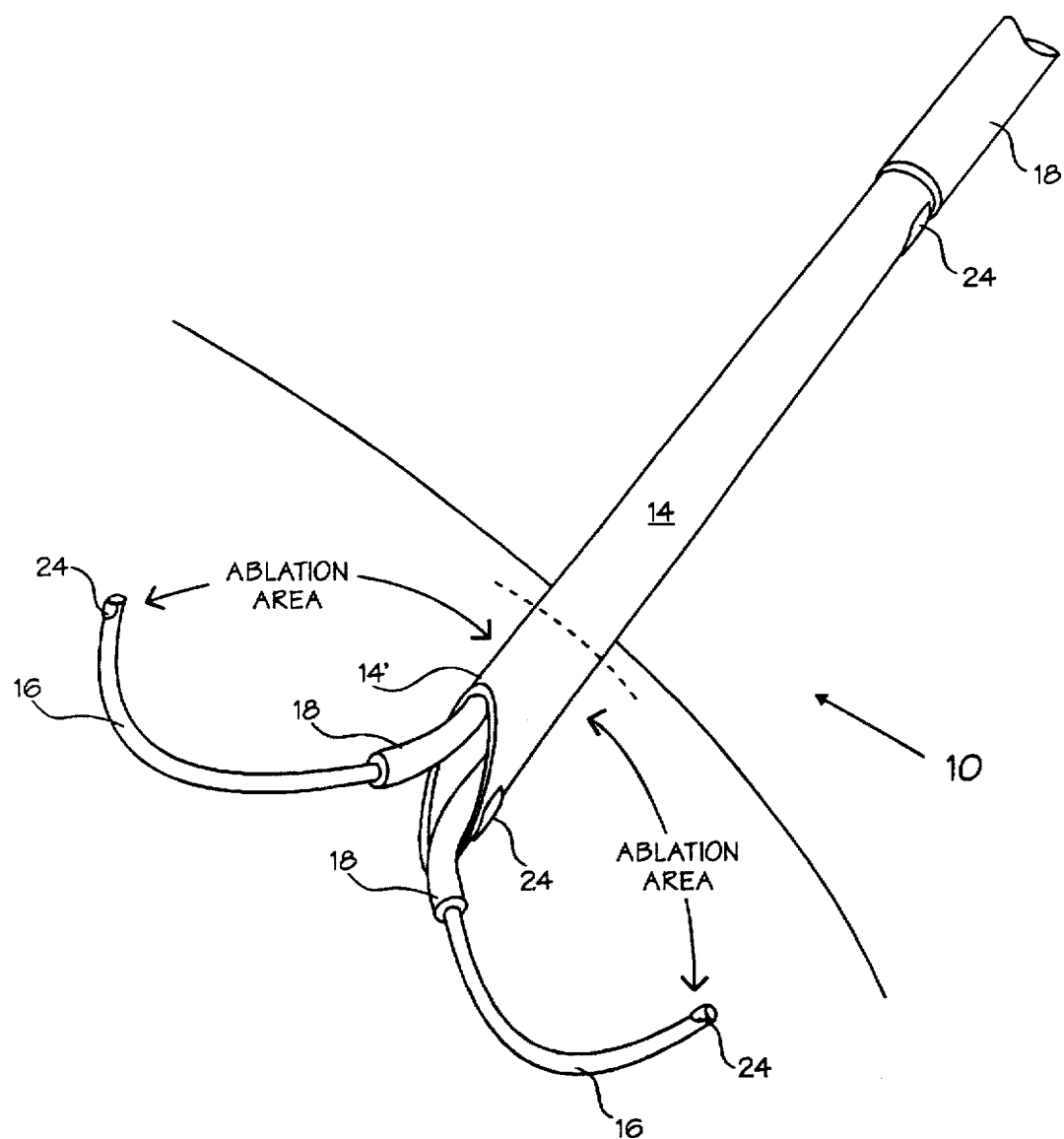
FIG. 3 is a perspective view of the multiple antenna ablation apparatus of the present invention with two secondary antennas deployed into the selected tissue mass.

In FIG. 3, two secondary antennas 16 are each deployed out of distal end 14' and introduced into selected tissue mass 28. Secondary antennas 16 form a plane and the area of ablation extends between the ablation surfaces of primary and secondary antennas 14 and 16. Primary antenna 14 can be introduced in an adjacent relationship to selected tissue mass 28. This particular deployment is particularly useful for small selected tissue masses 28, or where piercing selected tissue mass 28 is not desirable. Primary antenna 14 can be rotated, with secondary antennas 16 retracted into a central lumen of primary antenna 14, and another ablation volume defined between the two secondary antennas 16 is created. Further, primary electrode 14 can be withdrawn from its initial position adjacent to selected tissue mass 28, repositioned to another position adjacent to selected tissue mass 28, and secondary antennas 16 deployed to begin another ablation cycle. Any variety of different positionings may be utilized to create a desired ablation geometry for selected tissue mass of different geometries and sizes.

Figure 4:
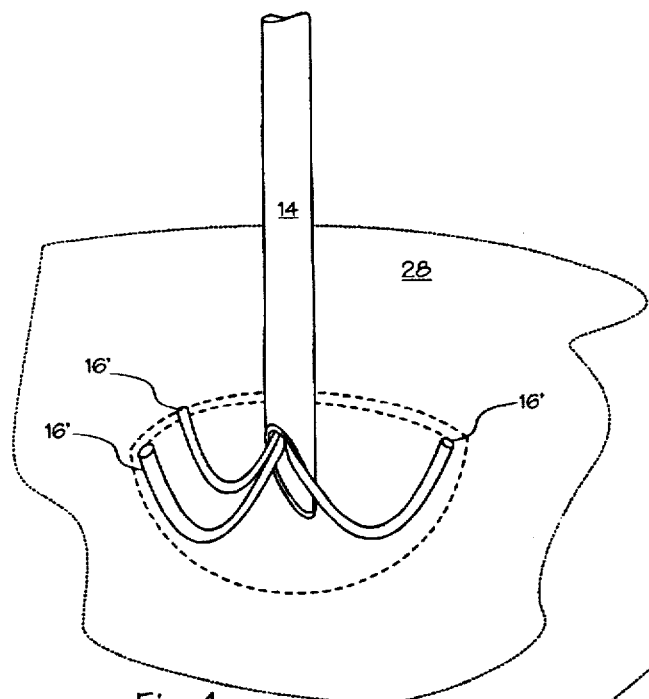
FIG. 4 is a perspective view illustrating the ablation created by the introduction of three secondary antennas into the selected tissue mass.

In FIG. 4, three secondary antennas 16 are introduced into selected tissue mass 28. The effect is the creation of an ablation volume without leaving non-ablated areas between antenna ablation surfaces. The ablation is complete.

Figure 5:
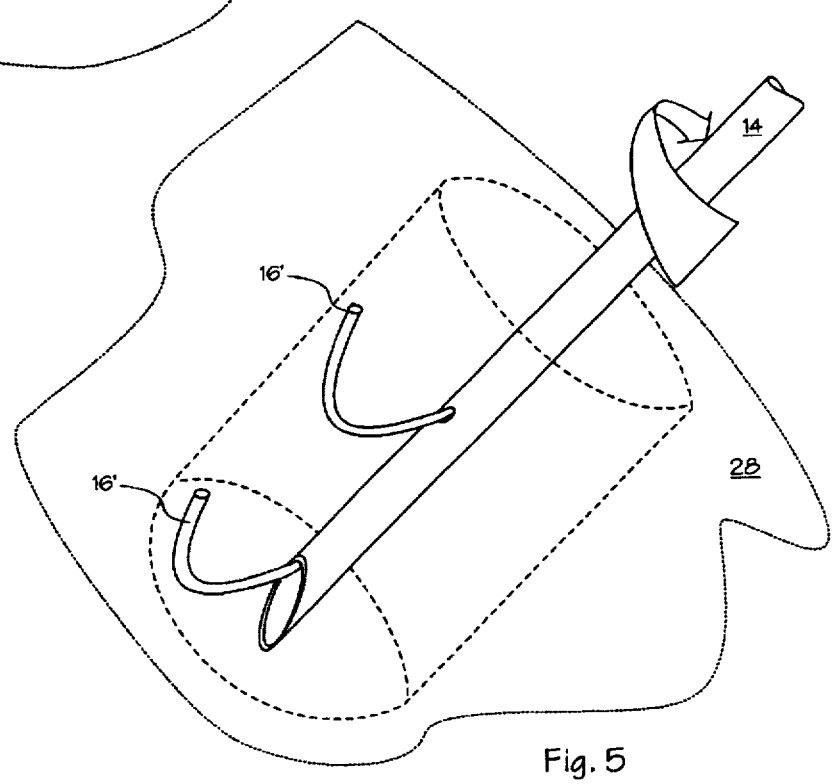
FIG. 5 is a perspective view illustrating the positioning of the multiple antenna ablation apparatus in the center of a selected tissue mass, and the creation of a cylindrical ablation.

Referring now to FIG. 5, a center of selected tissue mass 28 is pierced by primary antenna 14, secondary antennas 16 are laterally deployed and retracted, primary antenna 14 is rotated, secondary antennas 16 are deployed and retracted, and so on until a cylindrical ablation volume is achieved. Multiple antenna device 12 can be operated in the bipolar mode between the two secondary antennas 16, or between a secondary antenna 16 and primary antenna 14. Alternatively, multiple antenna device 12 can be operated in a monopolar mode.

Figure 6C:
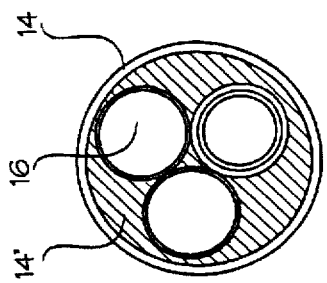
FIG. 6(c) is a cross-sectional view of the apparatus of FIG. 6(b) taken along the lines 6(c)—6(c).
Figure 6B:
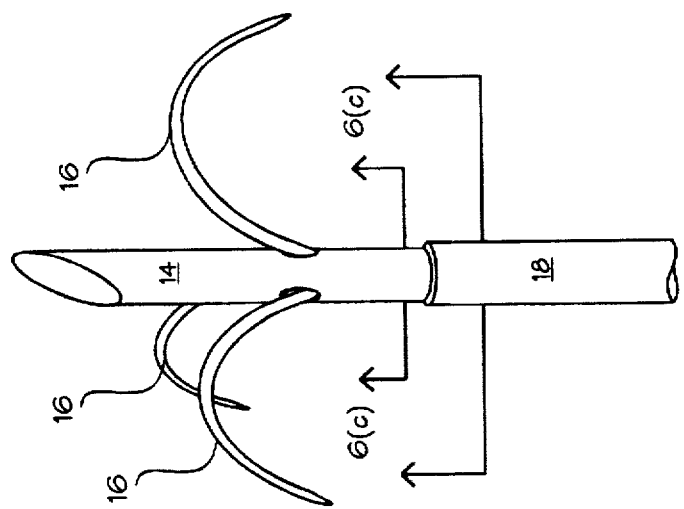
FIG. 6(b) is a perspective view of the multiple antenna ablation of the present invention illustrating three secondary antennas which provide a retaining and gripping function.
Figure 6A:
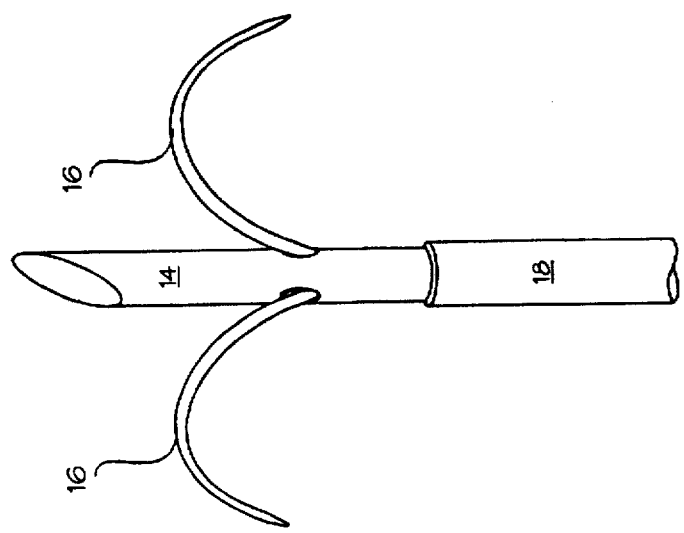
FIG. 6(a) is a perspective view of the multiple antenna ablation of the present invention illustrating two secondary antennas which provide a retaining and gripping function.

Secondary antennas 16 can serve the additional function of anchoring multiple antenna device 12 in a selected mass, as illustrated in FIGS. 6(a) and 6(b). In FIG. 6(a) one or both secondary antennas 16 are used to anchor and position primary antenna 14. Further, one or both secondary antennas 16 are also used to ablate tissue. In FIG. 6(b), three secondary antennas are deployed and anchor primary antenna 14.

FIG. 6(c) illustrates the infusion capability of multiple antenna device 12. Three secondary antennas 16 are positioned in a central lumen 14" of primary antenna 14. One or more of the secondary antennas 16 can also include a central lumen coupled to an infusion source. Central lumen 14" is coupled to an infusion source and delivers a variety of infusion mediums to selected places both within and outside of the targeted ablation mass. Suitable infusion mediums include but are not limited to, therapeutic agents, conductivity enhancement mediums, contrast agents or dyes, and the like. An example of a therapeutic agent is a chemotherapeutic agent.

Figure 8:
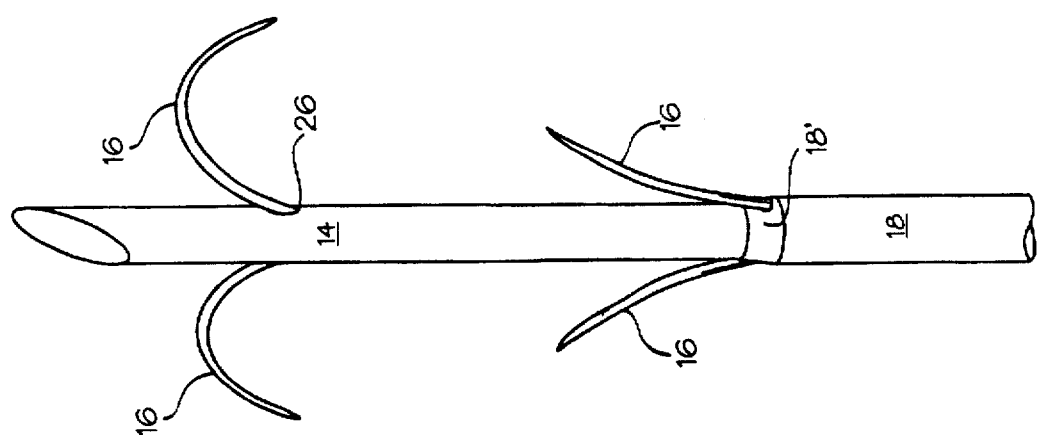
FIG. 8 is a perspective view of the multiple antenna ablation of the present invention illustrating the deployment of two secondary antennas from the primary antenna, and the deployment of three secondary antennas from the distal end of the insulation sleeve surrounding the primary antenna.
Figure 7:
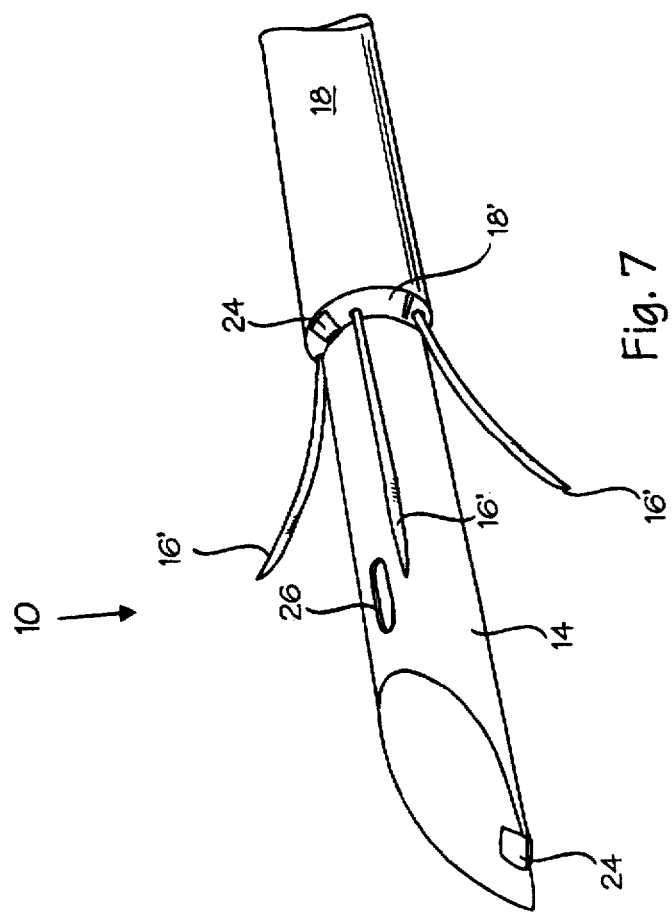
FIG. 7 is a perspective view of the multiple antenna ablation of the present invention illustrating the deployment of three secondary antennas from a distal end of the insulation sleeve surrounding the primary antenna.

As shown in FIG. 7 insulation sleeve 18 can include one or more lumens for receiving secondary antennas 16 which are deployed out of an insulation sleeve distal end 18'. FIG. 8 illustrates three secondary antennas 16 being introduced out of insulation sleeve distal end 18', and two secondary antennas 16 introduced through apertures 26 formed in primary antenna 14. As illustrated, the secondary electrodes introduced through apertures 26 provide an anchoring function. It will be appreciated that FIG. 8 shows that secondary antennas 16 can have a variety of different geometric configurations in multiple antenna device 12.

A feedback control system 29 is connected to energy source 20, sensors 24 and antennas 14 and 16. Feedback control system 29 receives temperature or impedance data from sensors 24 and the amount of electromagnetic energy received by antennas 14 and 16 is modified from an initial setting of electromagnetic energy output, ablation time, temperature, and current density (the "Four Parameters"). Feedback control system 29 can automatically change any of the Four Parameters. Feedback control system 29 can detect an impedance or temperature and change any of the Four Parameters. Feedback control system can include a multiplexer to multiplex different antennas, a temperature detection circuit that provides a control signal representative of temperature or impedance detected at one or more sensors 24. A microprocessor can be connected to the temperature control circuit.

The following discussion pertains particularly to the use of an RF energy source and RF multiple antenna device 12. It will be appreciated that devices similar to those associated with RF multiple antenna device 12 can be utilized with laser optical fibers, microwave devices and the like.

Figure 9:
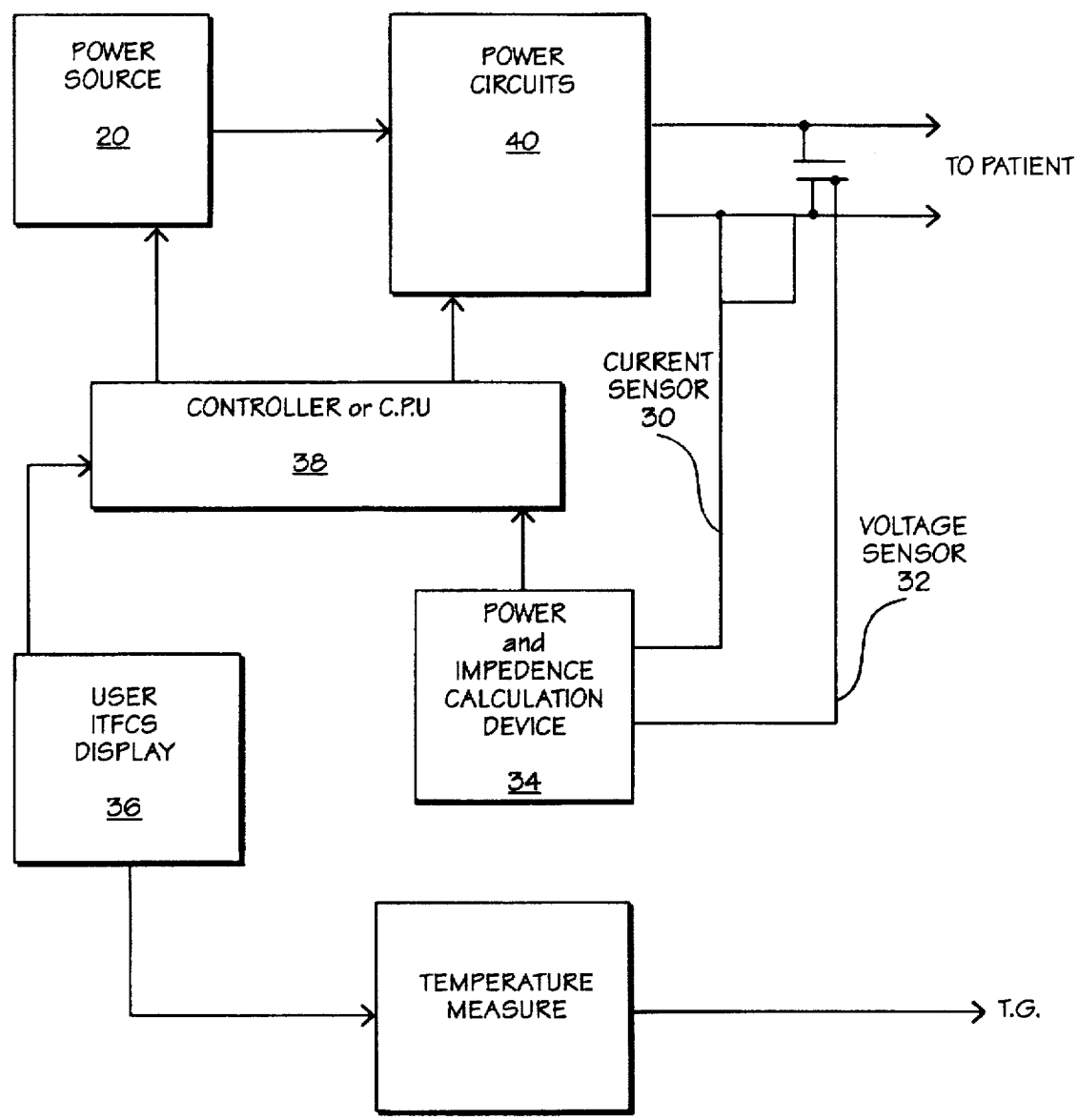
FIG. 9 is a block diagram illustrating the inclusion of a controller, energy source and other electronic components of the present invention.

Referring now to FIG. 9, all or portions of feedback control system 29 are illustrated. Current delivered through primary and secondary antennas 14 and 16 is measured by current sensor 30. Voltage is measured by voltage sensor 32. Impedance and power are then calculated at power and impedance calculation device 34. These values can then be displayed at user interface and display 36. Signals representative of power and impedance values are received by controller 38.

A control signal is generated by controller 38 thin is proportional to the difference between an actual measured value, and a desired value. The control signal is used by power circuits 40 to adjust the power output in an appropriate amount in order to maintain the desired power delivered at the respective primary and/or secondary antennas 14 and 16.

In a similar manner, temperatures detected at sensors 24 provide feedback for maintaining a selected power. The actual temperatures are measured at temperature measurement device 42, and the temperatures are displayed at user interface and display 36. A control signal is generated by controller 38 that is proportional to the difference between an actual measured temperature, and a desired temperature. The control signal is used by power circuits 40 to adjust the power output in an appropriate amount in order to maintain the desired temperature delivered at the respective sensor 24. A multiplexer can be included to measure current, voltage and temperature, at the numerous sensors 24, and electromagnetic energy is delivered between primary antenna 14 and secondary antennas 16.

Controller 38 can be a digital or analog controller, or a computer with software. When controller 38 is a computer it can include a CPU coupled through a system bus. On this system can be a keyboard, a disk drive, or other non-volatile memory systems, a display, and other peripherals, as are known in the art. Also coupled to the bus are a program memory and a data memory.

User interface and display 36 includes operator controls and a display. Controller 38 can be coupled to imaging systems, including but not limited to ultrasound, CT scanners, X-ray, MRI, mammographic X-ray and the like. Further, direct visualization and tactile imaging can be utilized.

The output of current sensor 30 and voltage sensor 32 is used by controller 38 to maintain a selected power level at primary and secondary antennas 14 and 16. The amount of RF energy delivered controls the amount of power. A profile of power delivered can be incorporated in controller 38, and a preset amount of electromagnetic energy to be delivered can also be profiled.

Circuitry, software and feedback to controller 38 result in process control, and the maintenance of the selected power that is independent of changes in voltage or current, and are used to change, (i) the selected power, including RF, microwave, laser and the like, (ii) the duty cycle (on-off and wattage), (iii) bipolar or monopolar electromagnetic energy delivery and (iv) infusion medium delivery, including flow rate and pressure of the cooling and infusion mediums. These process variables are controlled and varied, while maintaining the desired delivery of power based on temperatures monitored at sensors 24.

Figure 10:
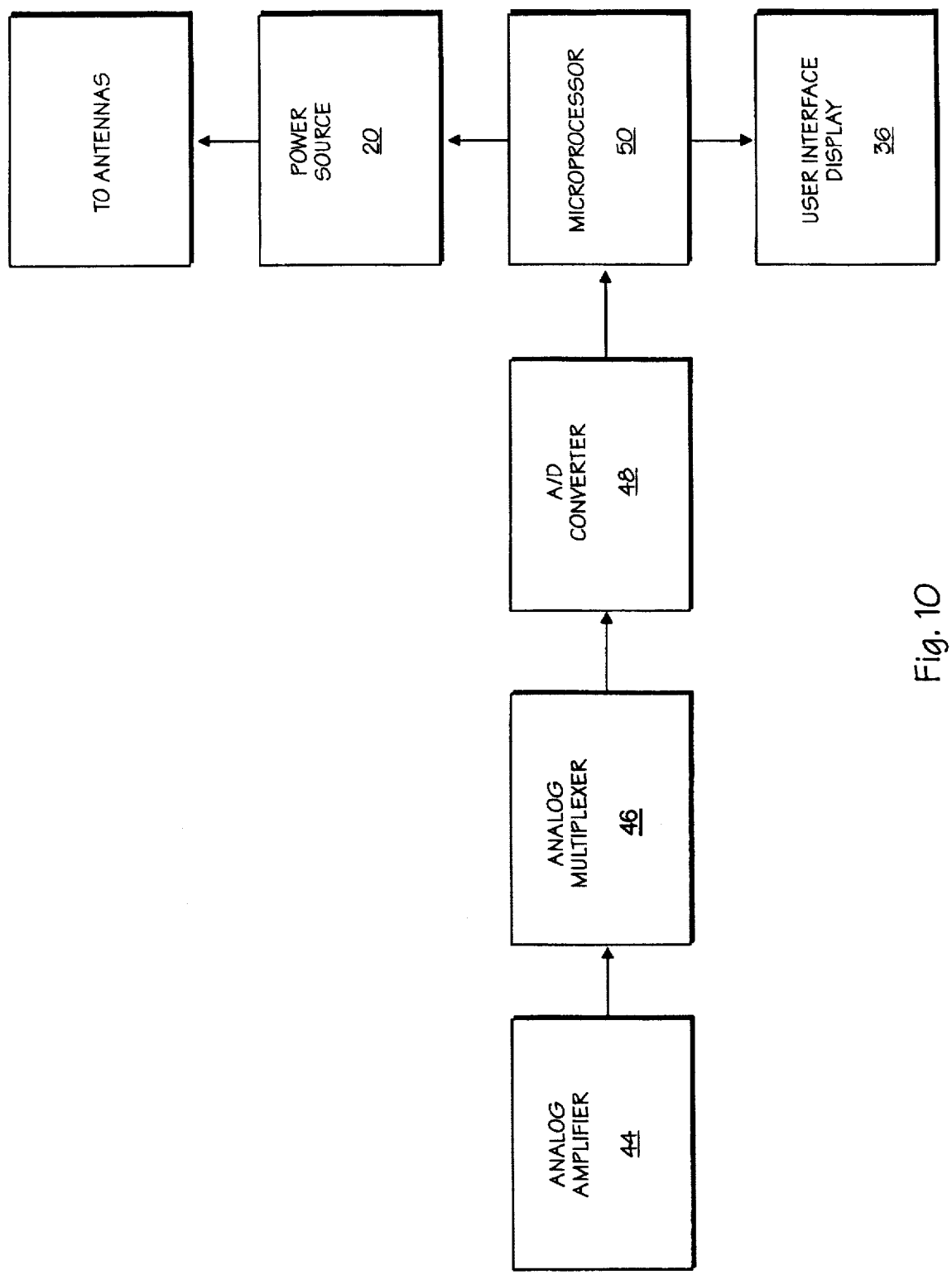
FIG. 10 is a block diagram illustrating an analog amplifier, analog multiplexer and microprocessor used with the present invention.

Referring now to FIG. 10, current sensor 30 and voltage sensor 32 are connected to the input of an analog amplifier 44. Analog amplifier 44 can be a conventional differential amplifier circuit for use with sensors 24. The output of analog amplifier 44 is sequentially connected by an analog multiplexer 46 to the input of A/D converter 48. The output of analog amplifier 44 is a voltage which represents the respective sensed temperatures. Digitized amplifier output voltages are supplied by A/D converter 48 to a microprocessor 50. Microprocessor 50 may be Model No. 68HCII available from Motorola. However, it will be appreciated that any suitable microprocessor or general purpose digital or analog computer can be used to calculate impedance or temperature.

Microprocessor 50 sequentially receives and stores digital representations of impedance and temperature. Each digital value received by microprocessor 50 corresponds to different temperatures and impedances.

Calculated power and impedance values can be indicated on user interface and display 36. Alternatively, or in addition to the numerical indication of power or impedance, calculated impedance and power values can be compared by microprocessor 50 with power and impedance limits. When the values exceed predetermined power or impedance values, a warning can be given on user interface and display 36. The delivery of RF energy can be reduced, modified or interrupted. A control signal from microprocessor 50 can modify the power level supplied by power source 36.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. An ablation apparatus, comprising:
   a multiple antenna device configured to be coupled to an energy source, the multiple antenna device including a primary antenna with a lumen and a longitudinal axis and a distal end sufficiently sharp to pierce tissue, and a secondary antenna at least partially positioned in the secondary antenna including a distal portion configured to be deployed from the lumen in a lateral direction relative to the longitudinal axis, wherein at least a part of a deployed secondary antenna distal portion has at least one radius of curvature;
   at least one cable configured to be coupled to the multiple antenna device; and
   a cooling element coupled to the primary antenna.

2. The apparatus of claim 1, wherein the primary antenna has an energy delivery surface with a length that is at least 20% of a length of an energy delivery surface of the secondary antenna.

3. The apparatus of claim 1, wherein the primary antenna has an energy delivery surface with a length that is at least one-third of a length of an energy delivery surface of the secondary antenna.

4. The apparatus of claim 1, wherein the primary antenna has an energy delivery surface with a length that is at least one-half of a length of an energy delivery surface of the secondary antenna.

5. The apparatus of claim 1, wherein two secondary antennas are provided and laterally deployed from the primary antenna, each of the primary and secondary antennas having an energy delivery surface to create an ablation volume between the energy delivery surfaces.

6. The apparatus of claim 1, wherein three secondary antennas are provided and laterally deployed from the primary antenna, each of the primary and secondary antennas having an energy delivery surface to create an ablation volume between the energy delivery surfaces.

7. The apparatus of claim 1, further comprising:
   an insulation sleeve positioned in a surrounding relationship around at least a portion of an exterior of the primary antenna.

8. The apparatus of claim 7, wherein the insulation sleeve is adjustably moveable along an exterior of the primary antenna.

9. The apparatus of claim 1, further comprising:
   an insulation sleeve positioned in a surrounding relationship around at least a portion of an exterior of the secondary antenna.

10. The apparatus of claim 9, wherein the insulation sleeve is adjustably moveable along an exterior of the secondary antenna.

11. The apparatus of claim 1, further including a ground pad electrode and the primary and secondary antennas operate in a monopolar mode.

12. The apparatus of claim 1, wherein the primary and secondary antennas are RF antennas.

13. The apparatus of claim 1, wherein the cooling element cools the primary antenna substantially only where the primary antenna has an ablation energy delivery surface.

14. The apparatus of claim 1, wherein the cooling element comprises:
   a structure positioned in an interior of the primary antenna including at least one channel configured to receive a cooling medium.

15. The apparatus of claim 14, wherein the cooling medium is recirculated through the channel.

16. The apparatus of claim 1, wherein the distal end of the primary antenna is open.

17. The apparatus of claim 1, wherein the distal end of the primary antenna is closed.

18. The apparatus of claim 1, wherein the cooling element is positioned in an interior of the primary antenna.

19. The apparatus of claim 1, wherein the cooling element is positioned at an exterior surface of the primary antenna.

20. The apparatus of claim 1, wherein the cooling element is positioned within a wall defining the primary antenna.

21. A method for creating an ablation volume in a selected tissue mass, comprising:
   providing an ablation device with a primary antenna, one or more deployable secondary antennas at least partially housed in a primary antenna lumen formed in the primary antenna, a cooling element coupled to the primary antenna and an energy source coupled to the antennas to deliver electromagnetic energy, the primary antenna including a distal end sufficiently sharp to pierce tissue and at least a portion of a deployed distal portion of the secondary antennas is configured to have at least one radius of curvature;
   inserting the primary antenna into the selected tissue mass;
   advancing at least one secondary antenna into the selected tissue mass from the primary antenna lumen in a lateral direction relative to a longitudinal axis of the primary antenna;
   cooling an energy delivery service of the primary antenna;
   delivering electromagnetic energy from one of the primary antenna energy delivery surface, a secondary antenna energy delivery surface or both to the selected tissue mass; and
   creating an ablation volume in the selected tissue mass.

22. The method of claim 21, wherein two secondary antennas, each having an energy delivery surface, are advanced from the primary antenna, and an ablation volume is created between the two secondary antennas energy delivery surfaces and the primary electrode energy delivery surface.

23. The method of claim 22, wherein the two secondary antennas are advanced out of a distal end of the primary antenna.

24. The method of claim 22, wherein the two secondary antennas are advanced out of separate ports formed in the primary antenna.

25. The method of claim 22, wherein the two secondary antennas are advanced from the primary antenna and define a plane.

26. The method of claim 21, wherein three secondary antennas are advanced from the primary antenna.

27. The method of claim 26, wherein each of the three secondary antennas and the primary antenna has an energy delivery surface, and an ablation volume is formed between the energy delivery surfaces of the antennas.

28. The method of claim 21, wherein the primary electrode has an energy delivery surface that is at least equal to 20% or more of an energy delivery surface of the secondary antenna.

29. The method of claim 21, wherein the primary electrode has an energy delivery surface that is at least equal to one-third or more of an energy delivery surface of the secondary antenna.

30. The method of claim 21, wherein the primary electrode has an energy delivery surface that is at least equal to one-half or more of an energy delivery surface of the secondary antenna.

31. The method of claim 21, wherein the primary and secondary antennas are operated in a mono-polar mode.

32. The method of claim 21, wherein the ablation device is operated in a bipolar mode.

33. The method of claim 21, wherein the ablation device is operated in a bipolar mode.

34. The method of claim 21, wherein an energy delivery surface of the primary antenna is cooled sufficiently to prevent the energy delivery surface from impeding out while electromagnetic energy is delivered to the selected tissue mass.

35. The method of claim 21, wherein an energy delivery surface of the primary antenna is cooled sufficiently and the selected tissue mass between the energy delivery surface of the primary antenna and an energy delivery surface of the secondary antenna is ablated without the primary antenna impeding out.

36. An ablation apparatus, comprising:
an introducer including a lumen, a distal portion and a distal end sufficiently sharp to penetrate tissue, the introducer having a distal portion and an energy delivery device coupled to an energy source;
a temperature monitoring device at least partially positioned in the introducer as the introducer is advanced through the tissue, the temperature monitoring device including the distal portion at least partially deployable from the introducer at a selected tissue site, wherein at least part of the temperature monitoring device distal portion has at least one radius of curvature when deployed from the introducer;
a cooling element coupled to the introducer; and
a cable coupling the energy source to the energy delivery device.

37. The apparatus of claim 36, further comprising:
a sensor coupled to the temperature monitoring device; and
a feedback control system coupled to the energy source and the sensor, wherein the feedback control system is responsive to a detected characteristic from the sensor and provides a delivery of energy output from the energy source to the energy delivery device.

38. The apparatus of claim 37, wherein the sensor is positioned at the distal portion of the temperature monitoring device.

39. The apparatus of claim 36, wherein the energy delivery device is an RF electrode and the energy source is an RF energy source.

40. The apparatus of claim 39, further comprising:
a sensor coupled to the RF electrode; and
a feedback control system coupled to the RF energy source and the sensor, wherein the feedback control system is responsive to a detected characteristic from the sensor and provides a delivery of energy output from the RF energy source to the RF electrode.

41. The apparatus of claim 40, wherein the sensor is a thermal sensor.

42. The apparatus of claim 40, wherein the sensor is an impedance sensor.

43. The apparatus of claim 39, further including
a second RF electrode at least partially positioned in the introducer as the introducer is advanced through tissue, the second RF electrode including a distal portion configured to be coupled to the RF energy source and deployable from the introducer at a selected tissue site, wherein at least a part of the second RF electrode distal portion has at least one radius of curvature when deployed from the introducer.

44. The apparatus of claim 36, wherein the energy delivery device is a laser energy delivery device and the energy source is a laser.

45. The apparatus of claim 44, further comprising:
a sensor coupled to the laser energy delivery device; and
a feedback control system coupled to the laser and the sensor, wherein the feedback control system is responsive to a detected characteristic from the sensor and provides a delivery of energy output from the laser to the laser energy delivery device.

46. The apparatus of claim 45, wherein the sensor is a thermal sensor.

47. The apparatus of claim 44, further including
a second laser energy delivery device at least partially positioned in the introducer as the introducer is advanced through tissue, the second laser energy delivery device including a distal portion configured to be coupled to the laser and deployable from the introducer at a selected tissue site, wherein at least a part of the second laser energy delivery device distal portion has at least one radius of curvature when deployed from the introducer.

48. The apparatus of claim 36, wherein the energy delivery device is a microwave antenna and the energy source is a microwave source.

49. The apparatus of claim 48, further comprising:
a sensor coupled to the microwave antenna; and
a feedback control system coupled to the microwave source and the sensor, wherein the feedback control system is responsive to a detected characteristic from the sensor and provides a delivery of energy output from the microwave source to the microwave antenna.

50. The apparatus of claim 49, wherein the sensor is a thermal sensor.

51. The apparatus of claim 48, further including
a second microwave antenna at least partially positioned in the introducer as the introducer is advanced through tissue, the second microwave antenna including a distal portion configured to be coupled to the microwave source and deployable from the introducer at a selected tissue site, wherein at least a part of the second microwave antenna distal portion has at least one radius of curvature when deployed from the introducer.

* * * * *

UNITED STATES PATENT AND TRADEMARK OFFICE
CERTIFICATE OF CORRECTION

PATENT NO. : 5,735,847  
DATED : April 7, 1998  
INVENTOR(S) : Edward J. Gough and Alan A. Stein Page 1 of 1

It is certified that error appears in the above-identified patent and that said Letters Patent is hereby corrected as shown below:

Column 11,  
Line 34, replace "secondary" with -- primary --.  
Line 34, between "antenna" and "including" insert -- and --.

Signed and Sealed this

Second Day of May, 2006

JON W. DUDAS  
*Director of the United States Patent and Trademark Office*